United States Patent
Ehrhardt et al.

[11] Patent Number: 6,136,242
[45] Date of Patent: Oct. 24, 2000

[54] PROCESS FOR THE PRODUCTION OF CYANURIC CHLORIDE MOLDINGS

[75] Inventors: Knut Ehrhardt, Hanau; Ralf Goedecke, Rodenbach; Rolf Moller, Babenhausen; Juan Garcia, Schoneck, all of Germany

[73] Assignee: Degussa-Huls AG, Frankfurt, Germany

[21] Appl. No.: 09/288,516

[22] Filed: Apr. 8, 1999

[30] Foreign Application Priority Data

Apr. 9, 1998 [DE] Germany ............ 198 16 026

[51] Int. Cl.[7] .................. D01D 5/26; D01F 9/08
[52] U.S. Cl. ................... 264/143; 264/177.13
[58] Field of Search ................ 264/143, 177.13

[56] References Cited

U.S. PATENT DOCUMENTS

| | | |
|---|---|---|
| 3,409,619 | 11/1968 | Kosel . |
| 4,351,644 | 9/1982 | Kriebitzsch . |
| 4,591,493 | 5/1986 | Klima et al. . |

FOREIGN PATENT DOCUMENTS

| | | |
|---|---|---|
| 0 036 943 A1 | 10/1981 | European Pat. Off. . |
| 0 416 584 A1 | 3/1991 | European Pat. Off. . |
| 1 266 308 | 4/1968 | Germany . |
| 2843379 | 8/1985 | Germany . |
| 196 42 449 | 4/1998 | Germany . |

*Primary Examiner*—Leo B. Tentoni
*Attorney, Agent, or Firm*—Pillsbury Madison & Sutro LLP

[57] ABSTRACT

The invention relates to a process for the production of cyanuric chloride moldings, particularly in rod or flake form. Cyanuric chloride melt is cooled in a pressure cell equipped with a die capable of strand formation, wherein solidification takes place in the channel or channels of the die. The solidified cyanuric chloride is pressed out of the die in strand form at a temperature of 140° C. or less, preferably 40 to 60° C., and reduced in size as required. The process reduces the sublimation which is otherwise conventional during solidification and cooling.

10 Claims, 1 Drawing Sheet

PROCESS FOR THE PRODUCTION OF CYANURIC CHLORIDE MOLDINGS

FIELD OF THE INVENTION

The invention relates to a process for the production of cyanuric chloride moldings, wherein the moldings are rod or flake-shaped, by cooling cyanuric chloride melt in a molding tool.

BACKGROUND OF THE INVENTION

It is known to convert cyanuric chloride in vapor form and obtained by trimerization of cyanogen chloride into solid fine-particle cyanuric chloride directly or via liquid cyanuric chloride:

The precipitation of pulverulent cyanuric chloride by desublimation of cyanuric chloride in vapor form may take place in externally cooled chambers or by introducing the cyanuric chloride vapor into a precipitation chamber with an inert gas and/or an inert coolant which evaporates in the precipitation process—see for example DE-PS 12 66 308 and U.S. Pat. No. 4,591,493. To obtain fine-particle cyanuric chloride from liquid cyanuric chloride the latter is sprayed into a precipitation chamber and cooled in the precipitation chamber with circulated inert cooling gases or by indirect cooling until the spray droplets precipitate in crystalline form—see for example DE 28 43 379. Considerable technical outlay for precipitation chambers and devices for recycling and cleaning process and waste gases is common to the processes.

In the processes which have been appreciated in the past and are based on the same principles, cyanuric chloride is always obtained in fine-particle form, generally with a maximum particle diameter substantially below 250 $\mu$m. Although such fine-particle products are advantageous as regards their high reactivity they have a number of drawbacks which make another product form desirable for many purposes.

The handling, such as feeding, storing and metering, of fine-particle cyanuric chloride poses particular problems because the corrosive and irritant properties accompany the conventional dust formation of fine-particle substances which requires extraction devices. Furthermore, cyanuric chloride is sensitive to hydrolysis, wherein hydrolysis products formed thereby can contaminate not only cyanuric chloride itself, but also subsequent products produced therefrom. Because of its high surface, cyanuric chloride is particularly accessible to hydrolysis. This also means that solid deposits in the dust removal devices and dust-carrying pipes can easily occur. Technically complex measures and/or fittings are required in order to prevent faults and eliminate those which have occurred.

A further drawback of fine-particle cyanuric chloride is the unsatisfactory flowability. Although this can be improved by the addition of free-flow auxiliary substances, such as silicas, the free-flow auxiliary substance reduces the product purity of the cyanuric chloride and optionally also that of the products produced from it. According to EP-A 0 416 584 the flowability of solid cyanuric chloride produced by desublimation or spray crystallization may also be improved without the addition of a free-flow auxiliary substance, by a shear treatment thereof in a kneader or mixer, particularly at 60 to 120° C.; the finely powdered nature of the cyanuric chloride is not, however, eliminated by this process as the average particle size of exemplary embodiments is in the range from approximately 10 $\mu$m to 40 $\mu$m.

The as yet unpublished German patent application 196 42 449.6 discloses flake and pellet-shaped cyanuric chloride moldings. These moldings may be produced by applying molten cyanuric chloride in drop or strip form to a surface and removing the heat of fusion by cooling the surface or contacting the melt applied to the surface with a coolant gas. A drawback of this process is that the device with the cooling belt must be designed in enclosed form. Furthermore, because of the high sublimation vapor pressure of cyanuric chloride in the vicinity of the solidification point and also above 100° C. considerable sublimation takes place and hence formation of fine-particle material.

SUMMARY OF THE INVENTION

Accordingly, the object of the present invention is to provide a further process for the production of cyanuric chloride moldings. The process should be simple to handle; furthermore it should also be possible to operate the process in such a way that no notable sublimation takes place.

A process has been found for the production of cyanuric chloride moldings by cooling cyanuric chloride melt in a molding tool which is characterized in that a pressure cell equipped with a single or multi-channel die which is capable of strand formation is filled with cyanuric chloride melt. The wall of the pressure cell and/or the die is cooled in such a way that at the start of or within the channels of the die, the orifice cross-section of which is substantially constant over the channel length, the temperature is below the melting point of cyanuric chloride and a temperature of 140° C. or less is reached at the outlet, solidified cyanuric chloride is pressed out of the die in strand form by the effect of force on the pressure cell and the strand is then reduced in size.

The pressure cell to be used may be designed in any way, as a pressurized feed container for example or a coolable cell connected to such a container and with a die integrated therein or fitted thereto. The pressure cell is equipped with a coolable die with one or more straight channels located therein, the orifice cross-section of which is substantially identical over the length of the channels. The term "substantially" means that the channel may be wider in the inlet region, e.g. to avoid edge abrasion or to facilitate the insertion of a ram. The die is coolable via the external wall and/or cooling channels located in the die, so as to remove the heat of fusion and latent heat of the cyanuric chloride. A feature of the process essential to the invention is the fact that the solidification of the cyanuric chloride takes place only in the channel or channels of the die, i.e. after final forming, and the material solidified in this way is pressed out of the die accompanied by further cooling. The channels must be uniformly designed from the inlet on the pressure cell side to the outlet of the strands because a plastic forming after the solidification of the cyanuric chloride proved not to be possible. Because of the lack of plastic formability of the solidified cyanuric chloride on the one hand and low viscosity of the cyanuric chloride melt and hence insufficient pressure build-up on the other hand the use of an extruder proved to be unsuitable.

The length of the die and/or the intensity of the cooling thereof are responsible for the temperature of the emerging strand(s). A lower outlet temperature and hence a lower sublimation vapor pressure of the solidified material is achieved by prolonging and/or intensifying the cooling. The sublimation vapor pressure falls from approx. 27 kPa at 150° C. to, for example, 6.3 kPa at 120° C. and 0.27 kPa at 60° C. Preferably the outlet temperature is below 140° C., particularly below 100° C. and particularly preferably in the range from 40 to 60° C. The compressive force required for discharge increases as the length increases. Although the compressive force decreases as the feed speed increases, the outlet temperature rises.

The one or more channels in the die may have any cross section, but a round, oval or rectangular cross section is preferred. Where the cross section is round, the diameter is generally in the range from 1 to 5 mm; channels with a rectangular cross section, i.e. slit-shaped channels in particular, are preferably 5 to 30 mm wide and 1 to 5 mm high.

DETAILED DESCRIPTION OF THE PREFERRED EMBODIMENTS

Figure 1:
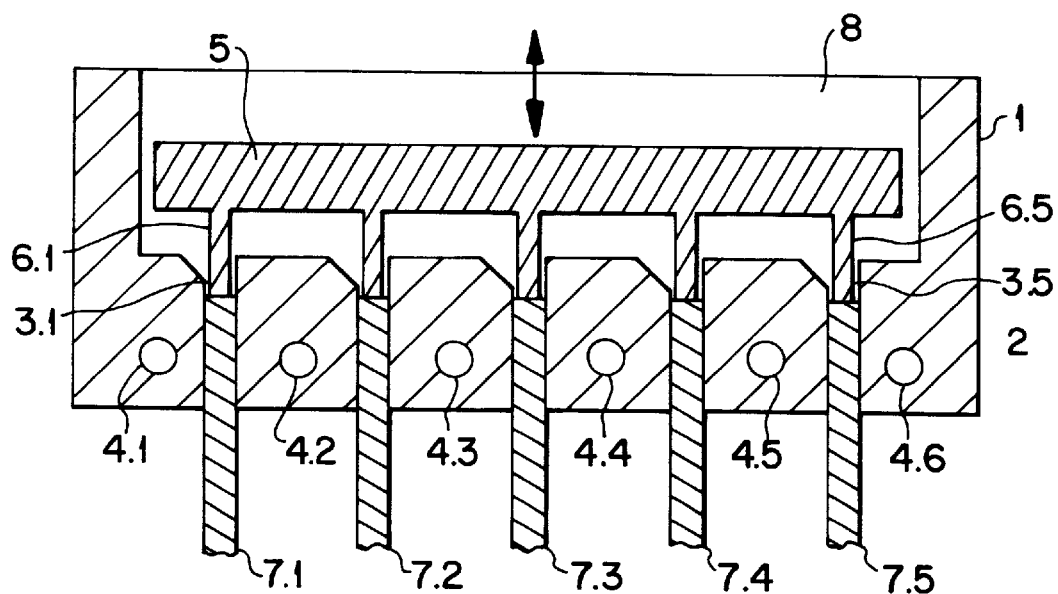
FIG. 1 is a schematic cross-sectional view of the lower part of a pressure cell of the invention, with a 5-channel die.

In diagrammatic form, FIG. 1 shows a cross section of a particularly appropriate embodiment of the lower part of a pressure cell with a 5-channel die: the die 2 with the channels 3.1 to 3.5 is arranged at the bottom of the pressure cell 1. The die comprises a cooling zone with cooling channels 4.1 to 4.6. A ram plate 5 with needles 6.1 to 6.5 which fit into the channels and are fixed to the ram plate is arranged in the pressure cell so that it can move vertically (lifting gear not shown). In the lowest position of the ram 5 the needles 6.1 to 6.5 extend only partially into the channels 3.1 to 3.5—with solidified cyanuric chloride strands 7.1 to 7.5 the lower part of the channels remains closed so that the cyanuric chloride melt 8 cannot escape from the pressure cell.

The person skilled in the art may build up the pressure required for discharge in any way. Examples which may be considered are high pressure piston pumps and diaphragm pumps. It is also possible to effect the pressure build-up and hence the discharge of the strand(s) by introducing a plunger by means of a screw press into a corresponding cylinder or directly into the channel or channels of the die. The use of a pressurized feed container to which the actual cell with the die is connected is preferred. The compression process may be continuous or intermittent. Depending on the length of the die and the desired feed speed the discharge pressure is generally in the range from 1 MPa to 100 MPa, particularly 1 MPa to 20 MPa and particularly preferably 1 to 5 MPa.

The reduction of the strands or strips emerging from the die into pieces, particularly ones with a length in the range from 5 to 30 mm, may take place using conventional crushing or cutting tools.

Cyanuric chloride moldings produced according to the invention are fully crystallized, stable in storage and transportable and largely dustless. The process according to the invention is distinguished in that the solidification of the cyanuric chloride melt and further cooling of the solid take place in a closed channel, by which means problems, such as formation of desublimate during solidification and cooling, are largely prevented.

EXAMPLES

Cyanuric chloride extrudates were produced in laboratory equipment. The device used for the purpose comprised a coolable cylindrical pressure cell of abrasion-resistant material with a capillary-shaped die integrated into the lower part. The capillary diameter was 5 mm. The cell was located in a pressure cell base with a chamber to receive the discharged strand. For discharge purposes a pressure needle was inserted into the cell by means of a screw press. The feed speed and length of the capillary were varied. The discharge pressure was recorded.

| Length of the capillary (mm) | Feed (mm/min) | Maximum pressure on discharge (MPa) |
| --- | --- | --- |
| 20 | 5 | 3 |
| 30 | 5 | 14 |
| 40 | 5 | 62 |
| 50 | 5 | 170 |
| 20 | 60 | 11 |
| 20 | 1000 | 2.5 |
| 20 | 1600 | 2.5 |

In all cases the temperature of the discharged strand was around/below 60° C.

What is claimed is:

1. A process for the production of cyanuric chloride moldings by cooling cyanuric chloride melt in a molding tool, comprising:

providing a pressure cell with a single or multi-channel die for strand formation;

filling the pressure cell with cyanuric chloride melt;

cooling a wall of at least one of the pressure cell and the die so that, at the start of or within the channels of the die, the channel cross-section, which is substantially constant over the channel length, has a temperature that is below the melting point of cyanuric chloride, and a temperature of 140° C. or less is present at the channel outlet;

pressing solidified cyanuric chloride out of the die in strand form by the effect of force on the pressure cell; and reducing the strand in size to form the cyanuric chloride moldings.

2. The process according to claim 1, wherein the channels of the die have a round, oval or rectangular orifice cross section.

3. The process according to claim 1, comprising applying force on the pressure cell by applying pressure to a feed connected to the pressure cell.

4. The process according to claim 1, comprising:

cooling the die so that solidified cyanuric chloride with a temperature in the range from 40 to 60° C. emerges from the die.

5. The process according to claim 1, comprising:

processing the solidified cyanuric chloride out of the pressure cell at a pressure of 1 to 20 MPa.

6. The process according to claim 1, comprising:

processing the solidified cyanuric chloride out of the pressure cell at a pressure of 1 to 5 MPa.

7. The process according to claim 2, wherein the channels of the die have a round orifice cross section with a diameter in the range from 1 to 5 mm.

8. The process according to claim 2, wherein the channels of the die have a rectangular orifice cross section with a width in the range from 5 to 30 mm and a height in the range from 1 to 5 mm.

9. The process according to claim 1, comprising applying force on the pressure cell by means of a high pressure piston pump.

10. The process according to claim 1, comprising applying force on the pressure cell by periodic introduction of a ram into the channels.

* * * * *